United States Patent
Pulnev

(10) Patent No.: US 6,641,608 B1
(45) Date of Patent: Nov. 4, 2003

(54) METHOD FOR RECONSTRUCTING BODY LUMENS

(75) Inventor: Sergei Appolonovich Pulnev, Sankt-Peterburg (RU)

(73) Assignee: Endovascular Technologies, Inc., Menlo Park, CA (US)

(*) Notice: Subject to any disclaimer, the term of this patent is extended or adjusted under 35 U.S.C. 154(b) by 1 day.

(21) Appl. No.: 10/057,261

(22) Filed: Oct. 24, 2001

Related U.S. Application Data

(63) Continuation of application No. 09/458,141, filed on Dec. 9, 1999, now Pat. No. 6,309,415, which is a continuation of application No. 08/860,462, filed on Jan. 22, 1998, now Pat. No. 6,007,574.

(51) Int. Cl.[7] ................................................. A61F 2/06
(52) U.S. Cl. ...................................... 623/1.15; 623/901
(58) Field of Search ............................ 623/1.11–1.15, 623/1.22, 1.5, 1.2, 1.51, 901

(56) References Cited

U.S. PATENT DOCUMENTS

| | | | | | | |
|---|---|---|---|---|---|---|
| 5,607,445 | A | * | 3/1997 | Summers | ................... | 606/198 |
| 5,653,747 | A | * | 8/1997 | Dereume | ................... | 623/1.15 |
| 6,007,574 | A | * | 12/1999 | Pulnev et al. | ............... | 623/1.15 |
| 6,309,415 | B1 | * | 10/2001 | Pulnev et al. | ............... | 623/1.22 |
| 6,319,277 | B1 | * | 11/2001 | Rudnick et al. | .......... | 623/1.13 |
| 6,342,067 | B1 | * | 1/2002 | Mathis et al. | ............... | 623/1.15 |
| 6,451,052 | B1 | * | 9/2002 | Burmeiser et al. | ......... | 623/1.16 |

\* cited by examiner

*Primary Examiner*—David H. Willse
*Assistant Examiner*—Suzette J. Jackson
(74) *Attorney, Agent, or Firm*—Fulwider Patton Lee & Utecht, LLP

(57) ABSTRACT

A stent shaped as a three-dimensional body which is formed by interlaced threads (1) arranged in multistart turns of a helical line. The threads (1) are arranged in at least two groups (2 and 3) of the helical turns featuring opposite senses of helix. The stent ends are established by sections (5) where the turns of one helical line merge into those of the other helical line, said sections appearing as a single length of the thread (1).

11 Claims, 2 Drawing Sheets

METHOD FOR RECONSTRUCTING BODY LUMENS

This is a continuation of application Ser. No. 09/458,141 filed Dec. 9, 1999 now U.S. Pat. No. 6,309,415, which is a continuation of application Ser. No. 08/860,462 filed Jan. 22, 1998, now U.S. Pat. No. 6,007,574.

TECHNICAL FIELD

The present invention relates in general to medicine and more specifically to surgery and can find predominant application for endoreconstruction of blood vessels and other hollow organs and structures of human body. The invention also enables one to carry out reconstruction of perforating lesions.

BACKGROUND ART

Modern medicine is capable of reconstructing blood vessels, ducts, and perforating lesions of human organs, using special framework-type devices named stents. Use of stents makes it possible to restore the natural function of an defected anatomical structure without having recourse to direct operative interference techniques.

In order to function as an effective and reliable endoprosthesis stents must possess a number of specific properties. First and foremost stents must provide unobstructed motion of body fluids through the implanted structure. Such stents must be very flexible and at the same time must be rigid enough to withstand the pressure exerted by walls of blood vessels or body cavities, with uniform pressure distribution over entire side surface of the stent. Moreover, the stent construction must be convenient for being transported to the zone of reconstruction and positioned there, as well as must not produce any or at least a minimal injurious effect upon the surrounding tissues in the course of implantation and further functioning.

One state-of-the-art hollow tubular stent is known to have end portions and a surface formed by a plurality of intersecting elastic elements at least part of which are interconnected at the stent ends (U.S. Pat. No. 733,665).

The stent can be of two different diametrical dimensions due to radial deformation of its elastic elements. Before being positioned at the place of reconstruction the stent is deformed so as to minimize its diametrical dimension. Then the stent is placed, in the deformed state, inside a transporting means by arranging it on a special setting bulb or balloon. Once the stent has been transported to the place of reconstruction the setting bulb or balloon is expanded so that the stent diameter is maximised.

It is due to its rigid construction that the stent withstands rather high pressure of the walls of the organ being prosthesized and provides for a uniform distribution of the resultant stresses over the prosthesized surface.

However, the stent in question features but lower elasticity due to a restricted axial deformation, which affects the quality of endoprosthesizing.

Another prior-art stent is known to be in the form of a hollow tubular springlike body made of a material having a shape memory effect (SME). Stents made from such a material are capable of restoring their shape upon a change in the temperature conditions.

The advantages of said stent are determined by the properties of the material it is made from that provides for complete restoration of the stent shape in the zone of reconstruction, as well as a possibility of its convenient withdrawal from the organ being prosthesized upon cooling of the stent. The procedure of the stent positioning is improved, too.

A variety of stent embodiments are possible. In particular, the stent may have a construction disclosed in the aforediscussed invention (U.S. Pat. No. 733,665).

One more stent embodiment presents its construction as a hollow tubular element established by the coils of a wire or the turns of a strip. The construction of such a stent is more elastic since the stent is deformable both radially and axially.

However, with this stent it is not always possible to provide and optimum value of the pitch of spring coils or of strip turns because with too a large pitch a uniform pressure distribution over the surface being prosthesized is affected, which may result in partial vessel stenosis, whereas in the case of too a small pitch stent implantation may cause hyperplasia of the intima of the vascular wall in the organ under reconstruction, as well as early thrombotic complications.

Still more stent of the prior art is known to appear as a three-dimensional tubular structure established by a number of interlaced rigid and/or elastic threads arranged in two groups along helical lines directed oppositely to each other. Ends of these helical threads are not connected to one another or to helical portions of other threads but are arranged loosely at both ends of the tubular structure.

The stent under consideration is elastic and easily deformable, and can be placed in a small-diameter delivery systems; besides, the stent provides for an adequate rigidity and a uniform pressure distribution over the surface being proshesized.

However, the presence of free ends of threads on the stent end faces can adversely affect the framework properties as a whole. To attain the required rigidity involves increasing the number of threads used, which is undesirable since this may cause intimal hyperplasia and early thrombotic complications. The ends of threads loosely arranged at the ends of the tubular structure can produce an injurious effect upon walls of a blood vessel; in addition, more complex devices are required to deliver the stent to a required location inside a body.

Known in the present state of the art is a stent in the form of a three-dimensional structure formed by interlaced threads arranged in multistart turns of a helical line (RU, A, 1,812,980). The turns form at least two groups featuring opposite senses of the helical line. The thread is made of a meterial featuring the SME. The ends of threads belonging to different groups are fixedly joined together on the end faces of the three-dimensional structure by, e.g., spot welding or splicing together.

The stent under discussion provides for a required rigidity and a uniform pressure distribution over the surface being prosthesized, as well as possesses elasticity.

It is due to joined together ends of threads on the stent end faces that its placing into a transporting system is simplified. The selected stent material ensures virtually complete restitution of its shape at the place of the prosthesis implantation.

However, an artificial joining of threads results in a local change of the physic-mechanical properties of the stent, which tells negatively on the rigidity and reliability of the stent construction as a whole. Moreover, the presence of artificial joints between the threads on the stent end faces gives one no way of attaining a maximum possible stent transformation which in turn places limitation on a possibility of its placing into a small-diameter delivery systems.

DISCLOSURE OF THE INVENTION

The present invention has for its principal object to provide a stent with a broad range of functional applications, possessing the required rigidity and elasticity, as well as a high degree of the shape transformation.

The foregoing object is accomplished due to the fact that in a stent shaped as a three-dimensional body which is formed by interlaced elastic threads arranged in multistart turns of a helical line and in at least two groups featuring opposite senses of the helix line, according to the invention, the ends of the three-dimensional body are established by the sections where the turns of one helical line merge into those of the other helical line, said sections appearing as a bend of a single thread segment.

Thus, instead of joining the threads at both ends of the stent by welding, soldering or other similar means, these ends are connected by curvilinear segments made of the same piece of thread. Hence similar physic-mechanical properties are retained in the entire stent volume, while the sections of the thread merging at the stent ends acquire the properties of a spring and become the functionally active construction elements. The stent ends formed by all the aforesaid sections of the thread bend are capable of withstanding the pressure of the walls of the anatomy under reconstruction, and the stent construction acquires the required rigidity so that the stent provides for a uniform pressure over the surface being prosthesized. In addition, it is due to their elastic properties that the section of the thread bend tend to restore their original shape after their having undergone deformation, thereby taking an active part in the process of the stent shape restoration.

The herein-proposed stent construction features the required elasticity due to a possibility of its radial and axial deformation under the action of small forces applied thereto.

The stent construction provides for high degree of the transformation of the stent shape. In the case of longitudinal stent deformation the threads slide with respect to one another, with the result that the angle of their mutual arrangement changes, the stent diameter decreases and becomes equal in length. Hence the stent diameter is much reduced, whereas its length changes but rather inconsiderably. High degree of the transformation cenables one to place different-dimension stents into a minimised-diameter delivery systems, a future that solves the problem of transporting stent to the place of reconstruction along both major and minor blood vessels.

To attain the maximum degree of the stent transformation with the required construction rigidity remaining unaffected, it is expedient that the turns of all the helical lines are made of a single thread segment. Such a stent possesses high elasticity and transformation ability due to a low interlacing density and a small number of threads. In addition, low interlacing density tells positively on the quality of endoreconstruction because it reduces reaction of the walls being prosthesized to a foreign body being implanted.

It is expedient in some cases that the stent features variable-pitch turns so as to provide different interlacing density as for the stent length with a view to, eg.g., high-rate formation of the neointima of the vessel walls on individual reconstruction areas.

It is practicable that the stent is shaped as three-dimensional body having variable cross-section diameter as for the length thereof, a future that makes it possible to obtain a stent shape adapted for endoreconstruction of defects of the various types and configurations.

Whenever it becomes necessary to obtain higher-density thread interlacing on a preset area, it is expedient that the stent is provided with additionally interwoven threads on said area. Such a stent is applicable for, e.g., reconstructing an aneurysms vessel.

It is expedient that the free thread ends are joined on the surface of the three-dimensional body, to the threads that form helical turns, and/or to one another, thus adding to the stent reliability.

It is expedient that on the sections of merging, the turns of one helical line merge into those of the helical line with the opposite sense of the helix. In this case, the radius of curvature of the merging section is increased, and such sections become more resilient.

A bend or curvilinear segment connecting two helical elements made from the same thread can have various shapes, e.g. a circular arc, a loop, or an U-shape. Those merging sections are most elastic which are shaped as circle arcs having a large radius of curvature.

In some instances it is expedient that the points of bending the threads on the merging sections are arranged in different transverse planes relative to the longitudinal body axis. This makes it possible to attain more compact arrangement of the stent ends during its transformation.

It is expedient that the stent is made of a material possessing a SME or of a superelastic material. Such stent possess a virtually complete degree of shape restitution.

It is expedient that, with a view to reducing its thrombogenicity, in some instances the stent may be provided with a biocompatible material.

No sources of information have been found by the Applicants that would contain any data on tecnical solutions idetical or equivalent to the device proposed herein. This, in the Applicants' opinion, renders the invention conforming to the condition of novelty (N).

Practical realisation of the specific features of the present invention imparts an important technical effect to the stent, consisting in that its required construction rigidity is attained along with high elasticity and transformation ability. The aforesaid novel feature of the present invention define, in the Applicants' opinion, conformity of the herein-proposed technical solution to the inventive step criterion (IS).

Practical use of the herein-proposed technical solution provides for a number of positive properties that follow:

Required construction rigidity and uniform pressure distribution over the surface being prosthesized;

High stent elasticity;

High degree of the shape transformation, which enables the stent to be placed into a minimum-diameter delivery systems;

Lower traumatogenicity of the stent implanting procedure;

Broad range of functional applications.

BRIEF DESCRIPTION OF THE DRAWINGS

In what follows the present invention will now be disclosed in a detailed description of some illustrative embodiments thereof with reference to the accompanying drawings, wherein:

Referring now to the accompanying Drawings FIG. 1 presents a stent of the present invention appearing as a three-dimensional body made of interlaced elastic threads 1 arranged in multistart turns along a helical line in two groups 2 and 3 featuring opposite senses of helix. The stent is made of a single segment of the thread 1 whose loose ends 4 are joined together and to the threads 1 of the groups 2 and 3 by interlacing. The stent ends are established by sections 5 of merging the turns of the thread 1 of the group 2 into the turns of the thread 1 of the group 3 and appear as a bend of the single segment of the thread 1. The bend of the thread 1 on the section 5 is shaped as a circle arc.

FIG. 2 presents a stent embodiment, wherein the bending points of the threads 1 on the merging sections 5 are situated in different transverse plane's a1, a2, and b1, b2 with respect to the longitudinal stent axis and are arranged in an alternating order. The bends of the threads 1 on the merging sections 5 are shaped as circle arcs. The stent is made from a single segment of the thread 1. Such an embodiment is preferable for large-diameter stents used in, e.g., endoprosthesizing the aorta, when a minimum diameter of the stent ends is to be provided in the deformed state, the required rigidity of the stent construction remaining unaffected. The diameter of this stent can be reduced more than tenfold throughout its entire length. The number of turns of the thread 1 and their pitch are preset proceeding from the required interlacing density, which is so selected that the area S of meshes established by the intersecting helical turns provides the required rigidity, whereas the meshes should be large enough not to cause hyperplasia of the intima of the walls under reconstruction or earlier thromboses complications.

FIG. 3 presents a stent embodiment, wherein the cross-sectional diameter in the central portion of the three-dimensional body is much larger than the cross-sectional diameters of the stent ends. The stent is spherial-shaped and is aimed at use as a filter for, e.g., preventing thromboembolism of the pulmonary artery. The merging sections 5 at the stent ends are loop-shaped.

FIG. 4 presents a stent embodiment intended for reconstructing, e.g., perforating injuries of the cardiac septa, or the open arterial duct. The stent has a minimum transverse diameter at the centre of the three-dimensional body and the maximum possible transverse diameters at its ends. The stent dimensions are so selected that its length exceeds the maximum diameter of a defect 6, and the diameter of the stent ends is such that the projection of the stent ends onto a wall 7 exceeds the area of the defect 6. The dotted line indicates the shape assumed by the stent in the strained state. The stent is positioned in the strained state through a perforation of the defect 6. Once installed the stent restores its original shape, whereby its end portions open up to their maximum diameter and are fixed outside the defect 6.

FIG. 5 presents a stent embodiment applicable in the case of an aneurysmal dilatation of a blood vessel. The stent is provided with the additionally interwoven threads 1 on a section 8, which features a higher interlacing density of the threads 1. This increase of density favorably influences neointima formation and is instrumental in blocking an aneurismal cavity 9 from a bloodstream in a vessel 10.

Figure 1:
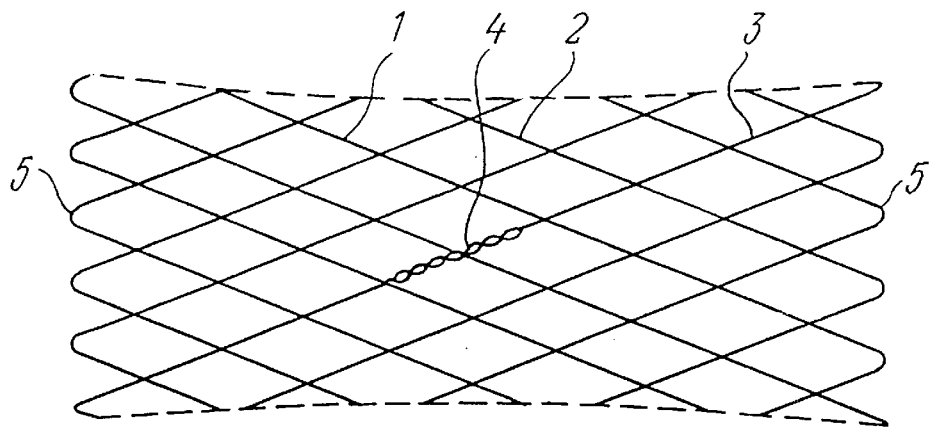
FIG. 1 is a general view of the proposal stent.
Figure 2:
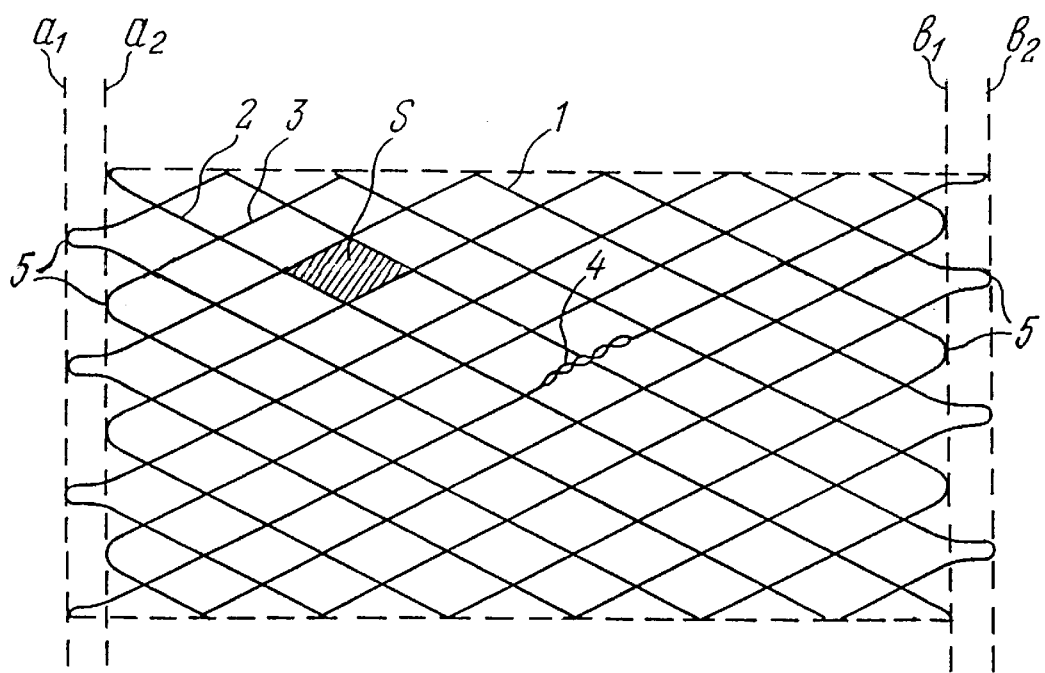
FIG. 2 shows an embodiment of the stent, wherein the bending points of threads on the merging sections are situated transverse planes relative to the longitudinal axis of the three-dimensional body.
Figure 3:
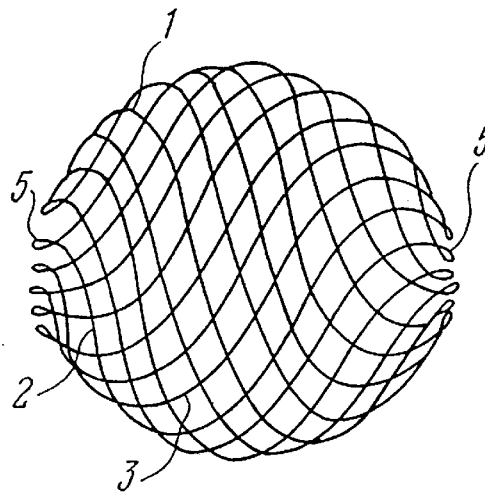
FIG. 3 shows another stent embodiment used as a filter.
Figure 4:
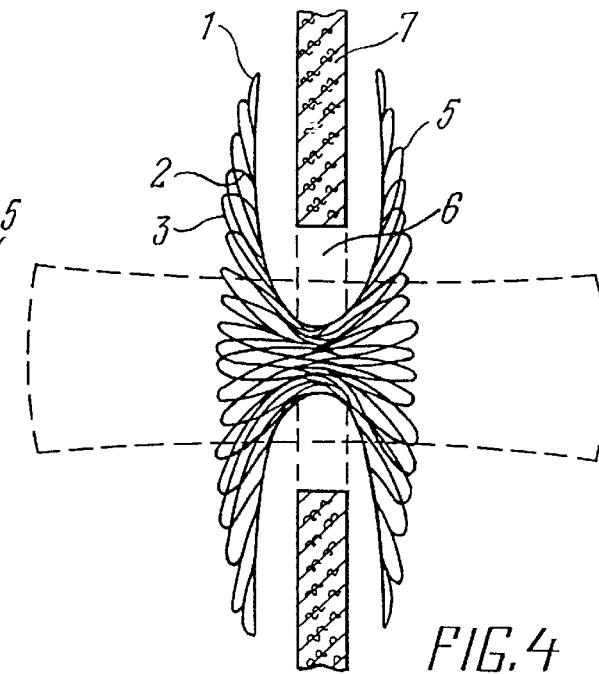
FIG. 4 shows one more stent embodiment aimed at endoreconstruction of perforating defects.
Figure 5:
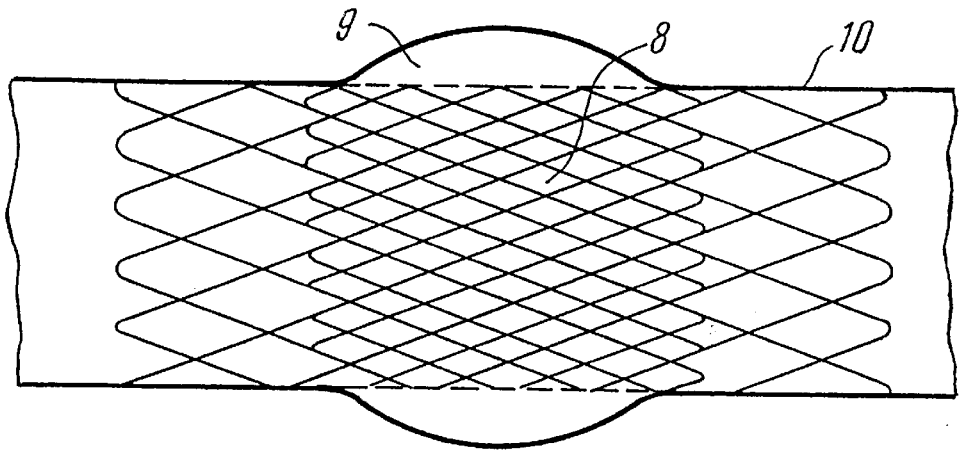
FIG. 5 shows a stent embodiment aimed at endoreconstruction of aneurysms vessels.

The herein-proposed stent operates as follows. A preliminary catheterization of the afferent passages is performed under aseptic conditions. A guide wire is inserted into the catheter, and the guide wire working end is placed outside the zone of reconstruction.

Then the catheter is withdrawn, whereupon the stent and the delivery system are fitted in succession onto the free guide wire end, said delivery system appearing as two coaxial catheters. Next the stent is deformed by applying slight longitudinal forces to the stent ends, after which the stent is placed into the free space of the outside catheter of the delivery system. Further on the assembled delivery system is brought to the place of endoreconstruction under fluoroscopy control and is released. The stent assumes its original shape and is fixed reliably in position.

Thus, the stent construction provides for its quick and convenient implantation in the preset zone of reconstruction.

INDUSTRIAL APPLICABILITY

The proposed invention is instrumental in attaining high-quality reliable endoprosthesizing of blood vessels, ducts, and perforating defects of the various organs, which is confirmed by good clinical effects attained in implantation of the stents in cases of occlusion-stenotic pathology of the blood vessels, vascular aneurysms, obstructions of the biliary ducts, and in portal hypertension (TIPS).

The aforelisted surgeries were conducted in St.Petersburg in 1992–1994 on the basis of the Central Roentgenology and Radiology Research Institute, the St.Petersburg State Medical Academy, as well on the basis of the Central Regional Clinical Hospital.

What is claimed is:

1. A method for reconstructing a body lumen using a reconstructive device having similar physic-mechanical properties along an entire length of the device, comprising:

gaining access to a body lumen of a patient;

advancing the reconstructive device to a reconstruction site;

deploying the reconstructive device at the reconstruction site; and configuring the reconstructive device at the reconstruction site in a manner to allow the entire length of the device to become functionally active construction elements capable of exhibiting similar physic-mechanical properties.

2. The method of claim 1, further comprising configuring the reconstructive device so that its length acquires the properties of a spring.

3. The method of claim 1, wherein the reconstructive device has a first end and a second end and further comprising configuring the reconstructive device so that its first and second ends acquire the properties of a spring.

4. The method of claim 1, further comprising forming the reconstructive device by crossing portions of the single thread, the crossing portions being configured to slide with respect to one another.

5. The method of claim 1, further comprising forming the reconstructive device by interlacing elastic thread portions.

6. The method of claim 5, further comprising configuring the elastic thread portions into multi-start turns of a helical line.

7. The method of claim 1, further comprising placing the reconstructive device at a stenosis.

8. The method of claim 1, further comprising placing the reconstructive device in the area of an aneurysm.

9. The method of claim 1, wherein the reconstructive device is self-expanding and further comprising allowing the reconstructive device to self-expand.

10. The method of claim 1, further comprising configuring the reconstructive device to have a low interlacing density pattern.

11. The method of claim 10, further comprising deploying the reconstructive device in a manner to reduce the reaction of the reconstruction site to the low interlacing density of the reconstructive device.

* * * * *

UNITED STATES PATENT AND TRADEMARK OFFICE
CERTIFICATE OF CORRECTION

PATENT NO. : 6,641,608 B1
DATED : November 4, 2003
INVENTOR(S) : Segi Appolonovich Pulnev It is certified that error appears in the above-identified patent and that said Letters Patent is hereby corrected as shown below:

Column 1,
Line 50, replace "maximised", with -- expanded to its maximal value --.

Column 6,
After line 36, and before line 37, add -- manufacturing a reconstructive device from a single thread --.
Line 44, after "site" add -- . -- (a period), and delete the remainder of lines 44-47 ending with "erties.".

Signed and Sealed this

Sixteenth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,641,608 B1  
APPLICATION NO. : 10/057261  
DATED : November 4, 2003  
INVENTOR(S) : Pulnev Page 1 of 1

It is certified that error appears in the above-identified patent and that said Letters Patent is hereby corrected as shown below:

On the cover of the printed patent replace the following phrase in the Related U.S. Application Data "application No. 08/860,462, filed on Jan, 22, 1998, now Pat. No. 6,007,574." with --U.S. Application No. 08/860,462, which is the National Stage of International Application No. PCT/RU94/00292 filed on Dec. 23, 1994, now Pat. No. 6,007,574--

On the face of the printed patent, the following new paragraph should appear immediately after the Related U S. Application Data section, as follows:

--Foreign Application Priority Data  
Dec. 28, 1993  [RU]  Russian Federation ............... 93058166--

Signed and Sealed this

Thirtieth Day of November, 2010

David J. Kappos  
*Director of the United States Patent and Trademark Office*